Oct. 22, 1968 R. PECOFF Plant Pat. 2,840
MYOPORUM PLANT
Filed Feb. 20, 1967
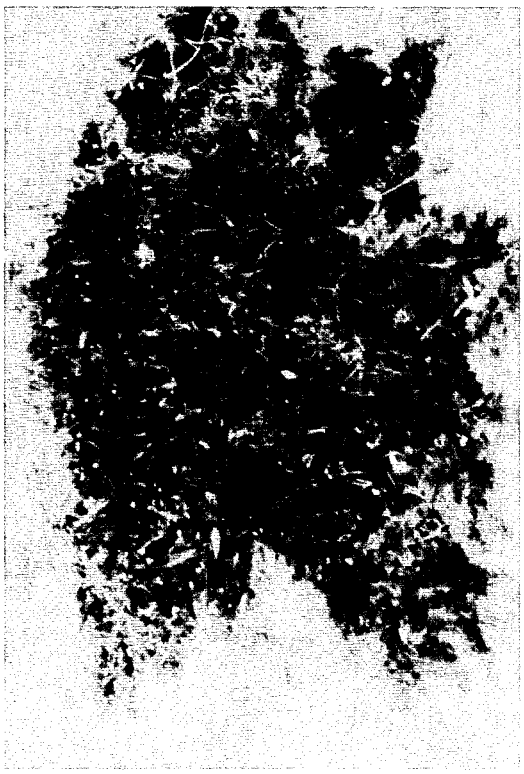
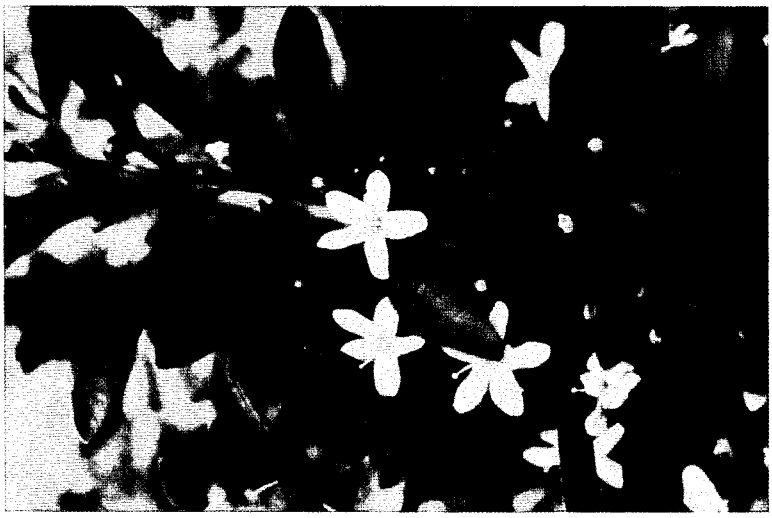
Inventor.
Ronald Pecoff
By: Robb & Robb
Attorneys.

United States Patent Office

Plant Pat. 2,840
Patented Oct. 22, 1968

2,840
MYOPORUM PLANT

Ronald Pecoff, 9200 Pershing Drive,
Playa Del Rey, Calif. 90291

Filed Feb. 20, 1967, Ser. No. 617,406
1 Claim. (Cl. Pit.—54)

The present invention relates to a new and distinct variety of Myoporum plant which was discovered by me as a newly found seedling growing in an enviroment dominated by halophites and surrounded by a white salt residue in a cultivated region containing a partially filled dry salt lake near Mitre, Victoria, Australia.

At the time of my discovery aforesaid, I was seeking new plant varieties suitable for ground cover or for general landscape use, and which were particularly salt resistant and suitable for growing in coastal salt soils, dredged ocean soils and calcarious sub-soils on hillsides, as well as in salt wind areas, and which were also resistant to hot desert temperatures, where such plants are especially useful for ground cover generally, and for erosion control and hillside stabilization. I have established that my newly found seedling eminently fulfills these objectives to a far greater extent than any other ground cover plant of which I am aware.

The parent of my new variety, which was growing nearby and is indigenous to Southern Australia, was an unnamed and unpatented variety botanically known as *Myoporum parvifolium,* which grows to a height of from 8 inches to 18 inches and spreads up to 4 feet wide, tends to mound in the center, and bears white flowers covering the plant as a solid white blanket.

My new seedling variety is definitely distinguished from the parent variety, as well as from all other Myoporum varieties of which I am aware, as evidenced by the following unique combination of characteristics which are outstanding in the new variety:

(1) A more compact, prostrate, dense, lower growing (2 inches to 3 inches), flat and more spreading (14 feet wide) plant habit in comparison with the parent variety which grows up to 18 inches tall and spreads only about 4 feet wide;

(2) Absence of die-back and less care required than most ground cover plants;

(3) Non-deciduous, glossy, dark green leaves which are larger than those of the parent variety, with the leaves being almost twice as long and being more serrated, with the serrations extending about half of each leaf while the leaves of the parent variety are serrated at the apex only, said leaves also having resinous glands and being sessile, while the glands of the parent variety are pellucid and have petioles;

(4) Greater resistance to insect and virus infestations;

(5) A more prolific rooting habit, even in clay and gravel soils;

(6) Larger white flowers, with purple spots on the corolla, with the flowers borne in scattered clusters, contrary to the small white flowers without spots and which blanket the plant of the parent variety and which are only about half the size;

(7) Greater tolerance to alkalinity and salinity, with a pH ranging from 9.5 to 10.0+ in a salt conductivity of from 10,000 to 30,000 p.p.m., as compared with a pH tolerance of from 6.5 to 7.5 for the parent variety; and (8) Greater tolerance to cold and hot weather, ranging from as low as 15° F. to as high as 140° F.

Asexual reproduction of my new variety by primary tip and secondary stem cuttings, as performed by me and on my behalf in Australia, as well as in California, shows that the foregoing characteristics and distinctions are fixed and established and come true through succeeding propagations.

The accompanying drawing shows a typical plant of my new variety, as well as specimens of the foliage and flowers on a somewhat enlarged scale, all as depicted in color as nearly true as it is reasonably possible to make the same in a color illustration of this character.

The following is a detailed description of my new variety, with color terminology in accordance with Wilson's Horticultural Colour Chart, published in collaboration with the Royal Horticultural Society, except where general color terms of ordinary dictionary significance are obvious:

Parentage: A seedling of an unnamed variety botanically known as *Myoporum parvifolium.*

Propagation: Holds its distinguishing characteristics through succeeding propagations by cuttings.

Locality where grown and observed: Playa Del Rey, Calif.

*Plant*

Form: Dwarf; compact; dense; prostrate; grows about 2 inches to 3 inches high and spreads about 14 feet wide as a tight, flat ground cover.

Habit: Vigorous; low growing; prostrate; rapid growing mat type ground cover.

Rooting: Prolific; roots along horizontal stems; roots well in clay and salt soils, as well as in sand dunes and on gravelly limestone hillsides, and if covered by erosion on hillsides, or by overburden, it will root well and produce new shoots which will grow and stabilize the soil.

Blooming Habit: In profuse clusters of 3 flowers per cluster, with the clusters scattered and rising vertically from the sessile leaves and stem union on flower stalks about 1 inch long.

Blooming season: From May through August in California.

Foliage:

*Leaves.*—Size—very large; about 2 inches long and about twice the size of the leaves of the parent variety. Quantity—abundant. Color—generally Spinach Green. New foliage: upper surface—Shiny Beetroot Purple, Plate 830/1 around ¼ of margin from apex, with remainder Anigosanthus Manglesii Green, Plate 960; under surface—Dull Anigosanthus Manglesii Green, Plate 960. Old foliage: upper surface—Shiny Anigosanthus Manglesii Green, Plate 960; under surface—Dull Magnolia Grandiflora Green, Plate 960/2. Shape—from lanceolate to spatulate. Texture—thick; fleshy; with resinous glands beneath the leaf; upper surface—glossy; under surface—rough. Margin—usually 7 serrations from apex to midpoint of margin. Aspect—concave, thick and spatulate, with red margins around upper half of leaf.

Disease and insect resistance: Very resistant to aphids, virus and die-back, as determined by comparison with other varieties grown in California in various locations where aphids, leaf scale and leaf virus were active and heavily infested other varieties of Myoporum plants, while there was no sign of infestation among my new variety.

*Flower*

Form: Campanulate; 5 lobed; large size; each flower has both pistillate and staminate organs.

*Size.*—From about 7/16 inch to 9/16 inch in diameter.

*Color.*—Top of Corolla—Imperial Purple, Plate 33/3. Bottom of corolla—Mauve, Plate 633/3.

Glandular dots in corolla—Beetroot Purple, Plate 830/1; arranged in two rows.

*Reproductive organs*

Stigma: Color—Imperial Purple, Plate 33/1.
Anthers: Color—Imperial Purple, Plate 33.

*Fruit*

Fruit: Bears succulent fruit in Australia, but does not fruit or seed in the United States.

*General observations*

Hardiness: Very hardy over temperature range of as low as 15° F. to as high as 140° F.

Use: Excellent ground cover for coastal salt soils and salt wind areas, and very useful for erosion control and hillside stabilization; it is the only known prostrate form of Myoporum plant; non-deciduous and remains compact and evergreen without die-back; requires no special care; suitable for general landscape use.

I claim:

1. A new and distinct variety of Myoporum plant, substantially as herein shown and described, characterized particularly as to novelty by the unique combination of a more compact, prostrate, dense, lower growing (2 inches to 3 inches), flat and more spreading (14 feet wide) plant habit in comparison with the parent variety which grows up to 18 inches tall and spreads only about 4 feet wide, absence of die-back and less care required than most ground cover plants, non-deciduous, glossy, dark green leaves which are larger than those of the parent variety, with the leaves being almost twice as long and being more serrated, with the serrations extending about half of each leaf while the leaves of the parent variety are serrated at the apex only, said leaves also having resinous glands and being sessile, while the glands of the parent variety are pellucid and have petioles, greater resistance to insect and virus infestations, a more prolific rooting habit, even in clay and gravel soils, larger white flowers, with purple spots on the corolla, with the flowers borne in scattered clusters, contrary to the small white flowers without spots and which blanket the plant of the parent variety and which are only about half the size, greater tolerance to alkalinity and salinity, with a pH ranging from 9.5 to 10.0+ in a salt conductivity of from 10,000 to 30,000 p.p.m., as compared with a pH tolerance of from 6.5 to 7.5 for the parent variety, and greater tolerance to cold and hot weather, ranging from as low as 15° F. to as high as 140° F.

No references cited.

ROBERT E. BAGWILL, *Primary Examiner.*